United States Patent
Labarthe et al.

(10) Patent No.: US 9,458,846 B2
(45) Date of Patent: Oct. 4, 2016

(54) PERISTALTIC PUMP FOR PUMPING A LIQUID AND METHOD FOR OPERATING A PERISTALTIC PUMP

(71) Applicant: Fresenius Vial SAS, Brezins (FR)

(72) Inventors: Sebastien Labarthe, Voiron (FR); Jean-Baptiste Berthier, Tullins-Fures (FR)

(73) Assignee: Fresenius Vial SAS, Brezins (FR)

( * ) Notice: Subject to any disclaimer, the term of this patent is extended or adjusted under 35 U.S.C. 154(b) by 403 days.

(21) Appl. No.: 14/351,593

(22) PCT Filed: Oct. 16, 2012

(86) PCT No.: PCT/EP2012/070500
§ 371 (c)(1),
(2) Date: Apr. 14, 2014

(87) PCT Pub. No.: WO2013/057109
PCT Pub. Date: Apr. 25, 2013

(65) Prior Publication Data
US 2014/0294610 A1    Oct. 2, 2014

Related U.S. Application Data

(60) Provisional application No. 61/549,768, filed on Oct. 21, 2011.

(30) Foreign Application Priority Data

Oct. 21, 2011 (EP) .................................. 111186093

(51) Int. Cl.
| | | |
|---|---|---|
| *F04B 43/08* | (2006.01) | |
| *F04B 43/12* | (2006.01) | |
| *A61M 5/142* | (2006.01) | |
| *A61M 5/168* | (2006.01) | |
| *A61M 5/36* | (2006.01) | |
| *F04B 49/08* | (2006.01) | |
| *F04B 49/10* | (2006.01) | |
| *F04B 49/00* | (2006.01) | |

(52) U.S. Cl.
CPC .......... *F04B 43/12* (2013.01); *A61M 5/14228* (2013.01); *A61M 5/16854* (2013.01); *A61M 5/16859* (2013.01); *A61M 5/365* (2013.01); *F04B 43/082* (2013.01); *F04B 49/00* (2013.01); *F04B 49/08* (2013.01); *F04B 49/10* (2013.01); *F04B 2205/03* (2013.01)

(58) Field of Classification Search
CPC .............. F04B 43/082; F04B 2205/03; F04B 2205/07; A61M 5/16831; A61M 5/16854; A61M 5/16859
See application file for complete search history.

(56) References Cited

U.S. PATENT DOCUMENTS

| 5,237,309 A | * | 8/1993 | Frantz ............... A61M 5/14216 340/679 |
|---|---|---|---|
| 5,292,306 A | | 3/1994 | Wynkoop et al. |
| 5,336,053 A | | 8/1994 | Wynkoop |
| 5,807,322 A | | 9/1998 | Lindsey et al. |
| 5,980,490 A | | 11/1999 | Tsoukalis |
| 2005/0145010 A1 | | 7/2005 | Vanderveen et al. |

FOREIGN PATENT DOCUMENTS

EP      0858812      8/1998

OTHER PUBLICATIONS

Written Opinion of the International Searching Authority dated Feb. 6, 2013, for International Application No. PCT/EP2012/070500.
International Search Report dated Feb. 6, 2013, for International Application No. PCT/EP2012/070500.
International Preliminary Report on Patentability dated Jan. 29, 2014, for International Application No. PCT/EP2012/070500.

* cited by examiner

*Primary Examiner* — Patrick Hamo
(74) *Attorney, Agent, or Firm* — Cook Alex Ltd.

(57) ABSTRACT

A peristaltic pump (1) for pumping a liquid comprises a flexible tube (2) for guiding the liquid to be pumped, a compression means (5) being actuatable for compressing the flexible tube (2), an upstream valve means (3) arranged in an upstream direction with respect to the compression means (5) and being actuatable to selectively open or close the flexible tube (2) upstream of the compression means (5), and a downstream valve means (4) arranged in a downstream direction with respect to the compression means (5) and being actuatable to selectively open or close the flexible tube (2) downstream of the compression means (5). A drive shaft (6) is provided which is rotatable for periodically actuating the compression means (5), the upstream valve means (3) and the downstream valve means (4). In addition, the peristaltic pump comprises a position detection means (8) for detecting the rotational position of the drive shaft (6) during actuation of the compression means (5), the upstream valve means (3) and the downstream valve means (4), a pressure sensor (7) being arranged between the upstream valve means (3) and the downstream valve means (4) for measuring a pressure signal (P) in the flexible tube (2) at a location between the upstream valve means (3) and the downstream valve means (4), and a control means (9) to control the operation of the peristaltic pump (1), the control means (9) being operative to detect a fault condition during the operation of the peristaltic pump (1) from a measured pressure signal (P). In a peristaltic pump (1) of this kind the control means (9), for detecting the fault condition, is operative to detect a peak (P1, P1') of the pressure signal (P) in a predefined interval (II) during rotation of the drive shaft (6) and to determine whether the fault condition is present or not by taking the signal value at the peak (P1, P1') and the location (T1, T1') of the peak (P1, P1') in the predefined interval (II) into account. In this way a peristaltic pump is provided allowing for an easy and reliable detection of a fault condition, in particular for detecting an empty-bag condition indicating that a bag supplying liquid to the flexible tube of the peristaltic pump is empty.

9 Claims, 5 Drawing Sheets

PERISTALTIC PUMP FOR PUMPING A LIQUID AND METHOD FOR OPERATING A PERISTALTIC PUMP

The invention relates to a peristaltic pump for pumping a liquid according to the preamble of claim 1 and a method for operating a peristaltic pump.

A peristaltic pump of this kind comprises a flexible tube for guiding the liquid to the pump, a compression means being actuatable for compressing the flexible tube, an upstream valve means arranged in an upstream direction with respect to the compression means and being actuatable to selectively open or close the flexible tube upstream of the compression means, and a downstream valve means arranged in a downstream direction with respect to the compression means and being actuatable to selectively open or close the flexible tube downstream of the compression means.

By means of the upstream valve means and the downstream valve means, the flexible tube can at two locations be selectively opened or closed to let the liquid pass through the flexible tube. By means of the compression means, the flexible tube can be compressed in a section between the upstream valve means and the downstream valve means such that, by sequential actuation of the compression means, the upstream valve means and the downstream valve means a liquid may be transported along the downstream direction within the flexible tube.

For actuating the compression means, the upstream valve means and the downstream valve means, conventionally a drive shaft carrying a number of cams acting onto the compression means, the upstream valve means and the downstream valve means is used. The drive shaft herein is rotatable and periodically actuates the compression means, the upstream valve means and the downstream valve means such that, in a periodic pumping operation, the liquid is pumped through the flexible tube.

A peristaltic pump of this kind is for example known from U.S. Pat. No. 5,807,322. In the peristaltic pump of U.S. Pat. No. 5,807,322, herein, a position detection means for detecting the rotational position of the drive shaft during actuation of the compression means, the upstream valve means and the downstream valve means is provided, which in combination with a pressure sensor being arranged between the upstream valve means and the downstream valve means and a control means to control the operation of the peristaltic pump is used to detect fault conditions during operation of the peristaltic pump, for example caused by an occlusion of the flexible tube upstream of the upstream valve means or downstream of the downstream valve means or caused by a so-called empty-bag condition indicating that a bag supplying liquid to the flexible tube is empty.

For detecting a fault condition, U.S. Pat. No. 5,807,322 proposes to observe a pressure signal output by the pressure sensor in certain intervals during the periodical pumping operation. For example, if a pressure signal is measured in an interval during the pumping operation in which the upstream valve means is opened and the downstream valve means is closed, the measured pressure signal is indicative of an upstream pressure. Vice a versa, if a pressure signal is measured while the upstream valve means is closed and the downstream valve means is opened, the measured pressure signal is indicative of a downstream pressure. Thus, by detecting changes in an upstream pressure and/or a downstream pressure it may be determined whether an occlusion of the flexible tube or an empty-bag condition is present preventing a correct pumping operation.

U.S. Pat. No. 5,807,322 proposes to relate a measured pressure signal to predetermined threshold values to for example detect an empty-bag condition indicating that a bag supplying liquid to the flexible tube is empty.

Setting such a threshold value, however, can be difficult because the conditions for pumping operation of the peristaltic pump may alter over time, caused for example by mechanical wear and tear of the flexible tube, aging of the tube and/or temperature changes during the pumping operation. A simple comparison between an actual measured pressure signal and a predetermined threshold value may thus not be sufficient and may lead to a false alarm or no alarm where an alarm actually should have been given.

It is an object of the invention to provide a peristaltic pump and a method for operating a peristaltic pump allowing for an easy and reliable detection of a fault condition, in particular for detecting a so-called empty-bag condition indicating that a bag supplying liquid to the flexible tube of the peristaltic pump is empty.

This object is achieved by a peristaltic pump having the features of claim 1.

In particular, the peristaltic pump is characterized in that the control means, for detecting the fault condition, is operative to detect a peak of the pressure signal in a predefined interval during rotation of the drive shaft and to determine whether the fault condition is present or not by taking the signal value at the peak and the location of the peak in the predefined interval into account.

The peristaltic pump in particular is designed to detect in a reliable manner an empty-bag condition and to issue an alarm if it is detected that a bag supplying liquid to the flexible tube is empty. For this, the control means is operative to detect, as fault condition, whether a bag connected to the tube upstream of the upstream valve means has ceased to supply liquid to the flexible tube.

The instant invention makes use of the idea to search for a peak of the pressure signal in a certain, predefined interval of the pumping operation, the interval herein being indicated by the position detection means issuing a position signal during rotation of the drive shaft. Because the pumping operation is periodic, the interval repeatedly occurs during repeated actuation of the compression means, the upstream valve means and the downstream valve means, and a peak of the pressure signal occurring within this interval should also repeatedly occur and should be approximately unchanged if the conditions during the pumping operation are unchanged. Thus, from a change of the peak of the pressure signal within the predefined interval it may be derived whether a change in the pumping operation has occurred and whether a fault condition is present or not.

The instant invention makes use of the surprising finding that, for reliably detecting a fault condition, not only the signal value of the pressure signal at the peak, but also the location of the peak within the predefined interval can be taken into account. In this regard it has been found that the signal value at the peak and the location at the peak may change with changing operation conditions, wherein such variations not necessarily are due to a fault condition such as an empty-bag condition, but may arise from a different set-up of the pump or a change in the mechanical conditions for example of the flexible tube. By hence taking into account both the signal value at the peak and the location of the peak within the predefined interval, influences of variations in the operation conditions being due to for example a change in the set-up or variations in the mechanical properties of the flexible tube may be computationally excluded or at least reduced, such that a fault condition resulting for example from an empty-bag condition can be identified with an increased reliability.

The predefined interval is indicated by the position detection means outputting a position signal indicating the position on the periodic rotation of the drive shaft. The predefined interval during which the peak of the pressure signal is detected herein may correspond to an interval in which, during a first portion of the interval, both the upstream valve means and the downstream valve means are closed and the compression means is actuated to compress the flexible tube. During the first portion of the predefined interval, hence, the pressure within the section of the flexible tube located between the upstream valve means and the downstream valve means increases due to the increasing compression applied to the flexible tube by the compression means. In a second portion of the predefined interval, then, the downstream valve means is opened to let the liquid contained in the section of the tube located between the upstream valve means and the downstream valve means flow downstream such that the pressure within the section of the flexible tube decreases leading to the forming of a peak within the predefined interval during normal operation of the peristaltic pump.

The position detection means may for example be constituted as an optical sensor acting together with an optical disc arranged on the drive shaft. The optical disc is rotated together with the drive shaft during operation of the peristaltic pump and comprises black (non-reflecting) and white (reflecting) faces causing a light signal to be selectively reflected or not during rotation of the drive shaft such that a periodic position signal is generated and output by the position detection means. Such position signal having the shape of a periodical wave form is used to indicate intervals during rotation of the drive shaft, hence correlating the pressure signal issued by the pressure sensor with a position of the drive shaft during actuation of the compression means, the upstream valve means and the downstream valve means.

For detecting a fault condition, in particular an empty-bag condition, a peak of the pressure signal in the predefined interval is detected and both the signal value at the peak and the location of the peak within the predefined interval are taken into account to determine whether a fault condition is present or not. In this regard, for determining whether the fault condition is present or not, an algorithm may be used to relate the signal value at the peak to the location of the peak within the predefined interval, hence determining a quantity which may then be compared in a reliable manner to a threshold value to determine whether the fault condition is present or not.

For example, in a specific implementation of such an algorithm the signal value at the peak may be multiplied by a factor and may be related to a reference value, wherein the factor depends on the location of the peak in the predefined interval and is computed taking the location of the peak in the predefined interval into account. Hence, using the factor the signal value at the peak is scaled depending on the location of the peak in the predefined interval to allow for an easy and reliable comparison to a threshold value.

The reference value may for example be determined using a mean value of the pressure signal during an interval of the rotation of the drive shaft during which the upstream valve means is opened and the downstream valve means is closed. Because the upstream valve means is opened and the downstream valve means is closed, the pressure within the section of the flexible tube between the upstream valve means and the downstream valve means in this interval at least approximately is equal to the pressure upstream of the upstream valve means. The pressure signal during the noted interval is, thus, indicative of an upstream pressure value which can be used to determine a reference value to determine a peak height of the peak of the pressure signal.

By then taking the difference between the signal value at the peak and the reference value to determine the peak height and by comparing this peak height to a threshold value it can be determined whether a fault condition is present or not.

Using the approach described above, in particular an empty-bag condition indicating that a bag supplying liquid to the flexible tube is empty can be determined in a reliable manner. To also detect other fault conditions, for example a downstream occlusion or an upstream occlusion, in addition an upstream pressure value may be determined from a mean value of the pressure signal during an interval of the rotation of the drive shaft during which the upstream valve means is opened and the downstream valve means is closed, and a downstream pressure value may be determined from a mean value of the pressure signal during an interval of the rotation of the drive shaft during which the upstream valve means is closed and the downstream valve means is opened. For detecting an occlusion of the flexible tube upstream of the upstream valve means, for example the upstream pressure value may be observed using the downstream pressure value as a reference value. Vice versa, for detecting an occlusion of the flexible tube downstream of the downstream valve means the downstream pressure value may be observed using the upstream pressure value as a reference.

By using the downstream pressure value as a reference for detecting an upstream occlusion and the upstream pressure value as a reference for detecting a downstream occlusion, influences of for example changing mechanical conditions on the measured pressure signal may be excluded. For example, the upstream pressure value includes and is affected by all relevant mechanical and temperature influences such that those are taken into account when using the upstream pressure value as a reference for determining the presence of a downstream occlusion.

The aspect of determining an upstream occlusion and/or a downstream occlusion may also be used independently from the scheme described before and being applicable in particular for detecting an empty-bag condition. A peristaltic pump making use of such an approach for detecting an upstream occlusion and/or a downstream occlusion may in general comprise the following features:
- a flexible tube for guiding the liquid to be pumped,
- a compression means being actuatable for compressing the flexible tube,
- an upstream valve means arranged in an upstream direction with respect to the compression means and being actuatable to selectively open or close the flexible tube upstream of the compression means,
- a downstream valve means arranged in a downstream direction with respect to the compression means and being actuatable to selectively open or close the flexible tube downstream of the compression means,
- a drive shaft being rotatable for periodically actuating the compression means, the upstream valve means and the downstream valve means,
- a position detection means for detecting the rotational position of the drive shaft during actuation of the compression means, the upstream valve means and the downstream valve means, a pressure sensor being arranged between the upstream valve means and the downstream valve means for measuring a pressure signal in the flexible tube at a location between the upstream valve means and the downstream valve means, and a control means to control the operation of the peristaltic pump, the control means being operative to detect a fault condition during the operation of the peristaltic pump from a measured pressure signal, wherein an upstream pressure value is determined from a mean value of the pressure signal during an interval of the rotation of the drive shaft during which the upstream valve means is opened and the downstream valve means is closed and a downstream pressure value is determined from a mean value of the pressure signal during an interval of the rotation of the drive shaft during which the upstream valve means is closed and the downstream valve means is opened, wherein for detecting an occlusion of the flexible tube upstream of the upstream valve means and/or downstream of the downstream valve means the upstream pressure value and the downstream pressure value are compared to each other.

The object is furthermore achieved with a method for operating a peristaltic pump for pumping a liquid having the features of claim 9. In such a method it is provided that the control means, for detecting the fault condition, detects a peak of the pressure signal in a predefined interval during rotation of the drive shaft and determines whether the fault condition is present or not by taking the signal value at the peak and the location of the peak in the predefined interval into account.

The advantages and advantageous embodiments described above with respect to the peristaltic pump are analogously applicable to the noted method.

The idea underlying the invention shall subsequently be described in more detail with reference to the embodiments shown in the figures. Herein.

Figure 1:
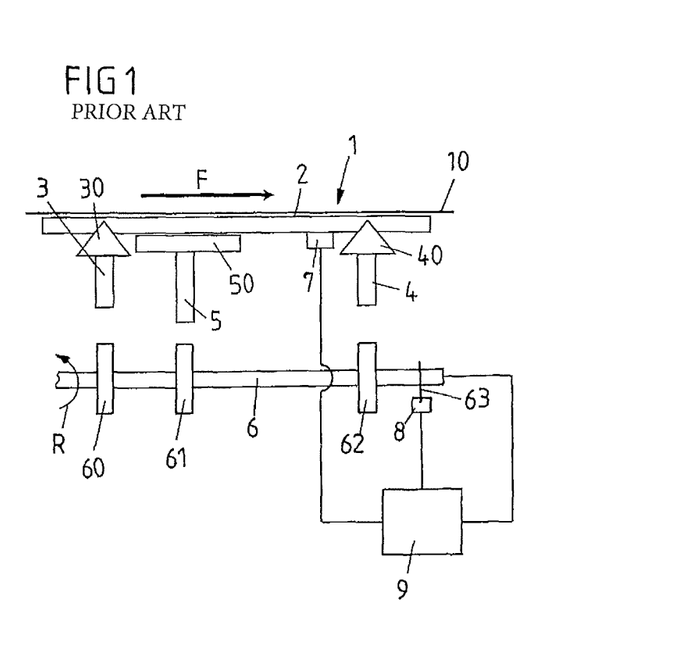
FIG. 1 shows a schematic view of a peristaltic pump.

FIG. 1 shows in a schematic view a peristaltic pump 1 comprising a flexible tube 2, a compression means 5, an upstream valve means 3 and a downstream valve means 4 interacting to transport a liquid contained in the tube 2 in a flow direction F.

The flexible tube 2 may for example be fabricated from a PVC material and hence is compressible in an easy and resilient manner in a direction perpendicular to the flow direction F. The upstream valve means 3 and the downstream valve means 4 act with a finger head 30, 40 onto the flexible tube 2 for selectively closing or opening the flexible tube 2 such that a liquid may pass through the flexible tube 2 or not. The compression means 5 is arranged, when viewed along flow direction F, between the upstream valve means 3 and the downstream valve 4 and acts with a finger head 50 onto the tube 2 for compressing the flexible tube 2 in a section located between the upstream valve means 3 and the downstream valve means 4.

To actuate the compression means 5, the upstream valve means 3 and the downstream valve means 4 in a sequential, periodic manner for transporting liquid through the tube 2 in the flow direction F a drive shaft 6 is provided which is rotatable in a direction of rotation R and carries three cams 60, 61, 62 acting onto the upstream valve means 3, the compression means 5 and the downstream valve means 4, respectively.

Figure 2:
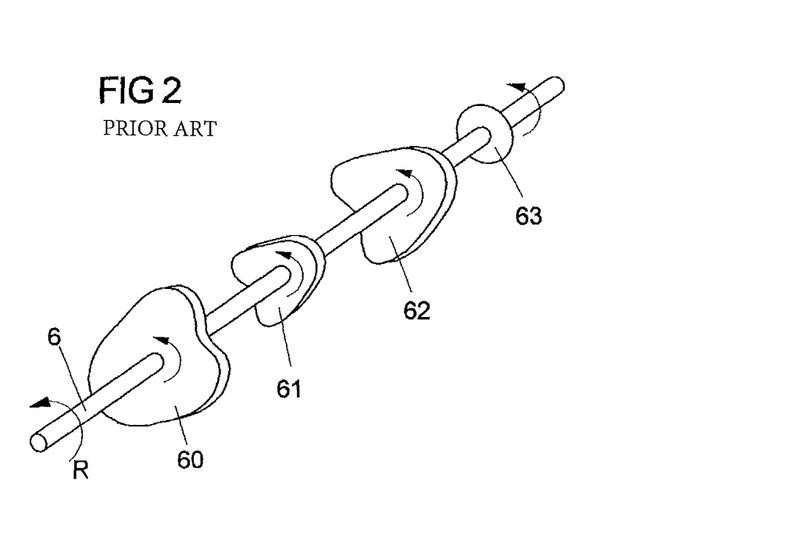
FIG. 2 shows a schematic, perspective view of a drive shaft carrying cams for actuating a compression means, an upstream valve means and a downstream valve means of the peristaltic pump.

A schematic, perspective view of the drive shaft 6 with the cams 60, 61, 62 mounted thereon is shown in FIG. 2 and is known per se for example from U.S. Pat. No. 5,807,322.

When operating the peristaltic pump 1, the compression means 5, the upstream valve means 3 and the downstream valve means 4 are actuated in a continuous manner by rotating the drive shaft 6, causing the liquid contained in the flexible tube 2 to be transported in the flow direction F. The flexible tube 2 in this regard rests against and is held in a support plate 10 (possibly arranged on a door of a housing of the peristaltic pump) serving as a support with respect to which the compression means 5 for compressing the flexible tube 2 and the upstream valve means 3 and the downstream valve means 4 for selectively opening or closing the flexible tube 2 may be moved.

Between the upstream valve means 3 and the downstream valve means 4 pressure sensor 7 is located being in contact with the flexible tube 2 for measuring a pressure signal at the flexible tube 2 indicative of the pressure within the flexible tube 2.

An optical disc 63 is mounted on the drive shaft 6 serving as a signal source for a position detection means 8. The optical disc 63 may for example comprise a number of black (non-reflective) and white (reflective) faces which selectively reflect a light signal such that the position detection means 8 outputs a position signal indicating the rotational position of the drive shaft 6.

In addition, a control means 9 is provided for controlling the operation of the drive shaft 6 and in addition evaluating a pressure signal output from the pressure sensor 7 and a position signal output from the position detection means 8 to for example detect fault conditions during operation of the peristaltic pump 1.

A general set-up of this kind is for example known from U.S. Pat. No. 5,807,322 which shall be incorporated herein by reference.

Referring now to FIGS. 3 to 10A, 10B, subsequently the principle operation of the peristaltic pump 1 shall be described. Herein, different states of the peristaltic pump 1 (FIGS. 3, 4A-10A) as well as pressure signals P and position signals O associated with such different states of the peristaltic pump 1 (FIGS. 4B-10B) are shown, a change of state of the peristaltic pump 1 always being accompanied by a change in the pressure signal P as measured by the pressure sensor 7.

In each case, the pressure signal P and the position signal O are shown in a diagrammatic view over time (in seconds). The pressure signal P being associated with the particular state of the peristaltic pump 1 is highlighted using a bold line.

Figure 3:
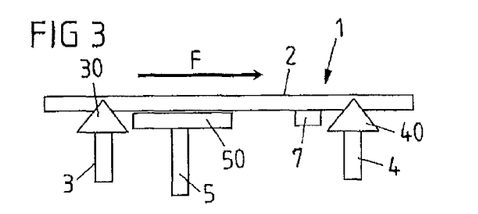
FIG. 3 shows the peristaltic pump in a first state.

In a first state of the peristaltic pump 1, shown in FIG. 3, the upstream valve means 3 and the downstream valve means 4 both are in a closed position hence closing the flexible tube 2 and preventing a flow through the flexible tube 2. In this first state, the compression means 5 does not act onto the flexible tube 2 and, hence, does not compress the flexible tube 2.

Figure 4A:
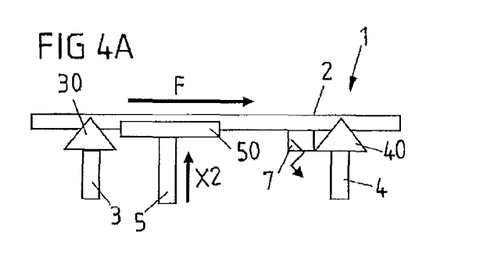
FIG. 4A shows the peristaltic pump in a second state.
Figure 4B:
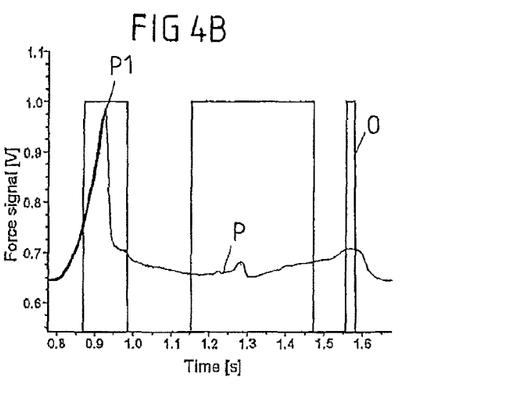
FIG. 4B shows a pressure signal associated with the second state.

In a second state, shown in FIG. 4A, the upstream valve means 3 and the downstream valve means 4 remain in their closed position, while the compression means 2 is moved in a direction X1 to act onto the flexible tube 2 and to compress the flexible tube 2 in its section between the upstream valve means 3 and the downstream valve means 4. As shown FIG. 4B, due to the compression of the flexible tube 2, the pressure signal P rises up to a peak P1.

Figure 5A:
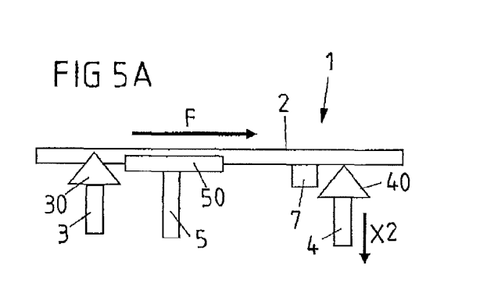
FIG. 5A shows the peristaltic pump in a third state.
Figure 5B:
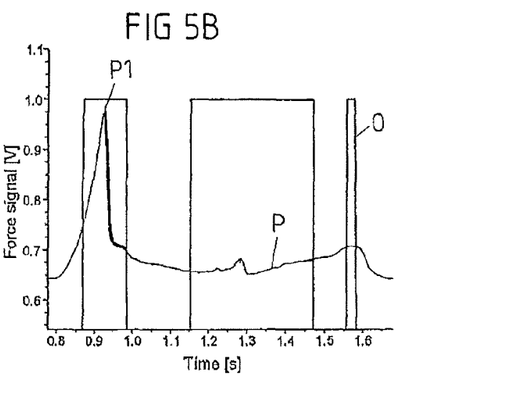
FIG. 5B shows a pressure signal associated with the third state.

In a third state of the peristaltic pump 1, shown in FIG. 5A, the upstream valve means 3 and the compression means 5 remain in their position, while the downstream valve means 4 is opened by moving the finger head 40 in a direction X2 to let liquid contained in the flexible tube 2 between the upstream valve means 3 and the downstream valve means 4 flow in the flow direction F downstream. As visible in FIG. 5B, this leads to a drop of the pressure signal P.

Figure 6A:
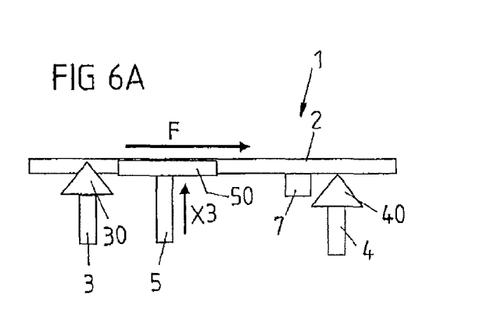
FIG. 6A shows the peristaltic pump in a fourth state.
Figure 6B:
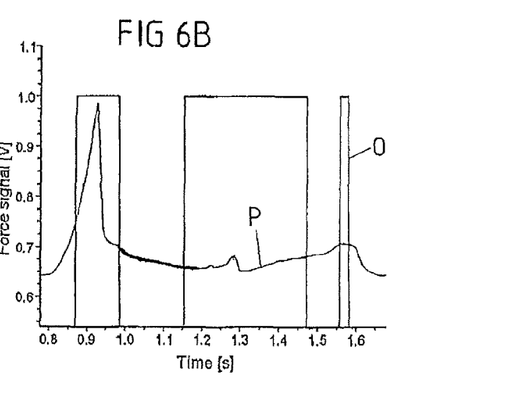
FIG. 6B shows a pressure signal associated with the fourth state.

In a forth state of the peristaltic pump 1, shown in FIG. 6A, the compression means 5 is moved in a direction X3 to further compress the flexible tube 2 to support the transportation of liquid in the flow direction F. During this action of the compression means 5, the pressure signal P drops only slightly (see FIG. 6B).

Figure 7A:
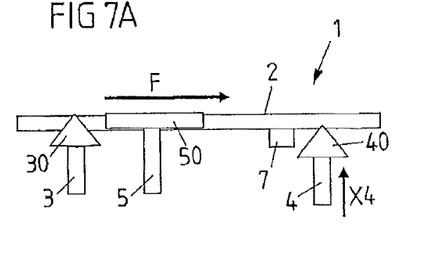
FIG. 7A shows the peristaltic pump in a fifth state.
Figure 7B:
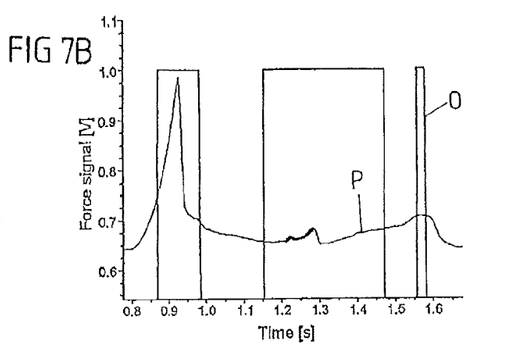
FIG. 7B shows a pressure signal associated with the fifth state.

In a fifth state, shown in FIG. 7A, the downstream valve means 4 is closed and for this is moved in a direction X4, leading to a small rise in the pressure signal P (see FIG. 7B).

Figure 8A:
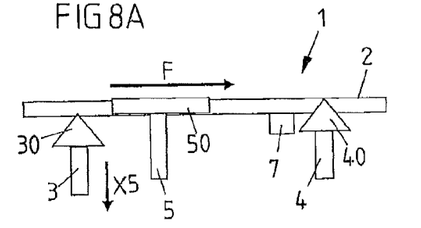
FIG. 8A shows the peristaltic pump in a sixth state.
Figure 8B:
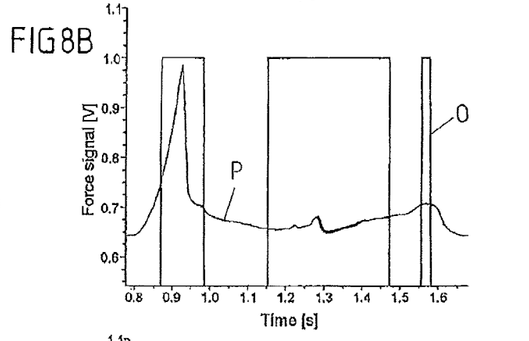
FIG. 8B shows a pressure signal associated with the sixth state.

In a sixth state, shown in FIG. 8A, the upstream valve means 3 is opened and for this is moved with its finger head 30 in a direction X5 to let liquid pass into the section of the flexible tube 2 between the upstream valve means 3 and the downstream valve means 4, while the compression means 5 and the downstream valve means 4 remain in their previously assumed position. The opening of the upstream valve means 3 causes a slight decrease in the pressure signal P, as shown in FIG. 8B.

Figure 9A:
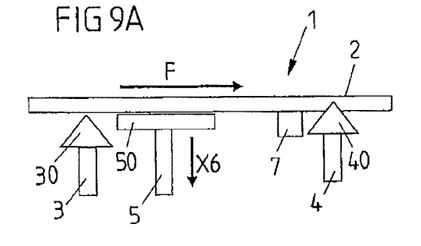
FIG. 9A shows the peristaltic pump in a seventh state.
Figure 9B:
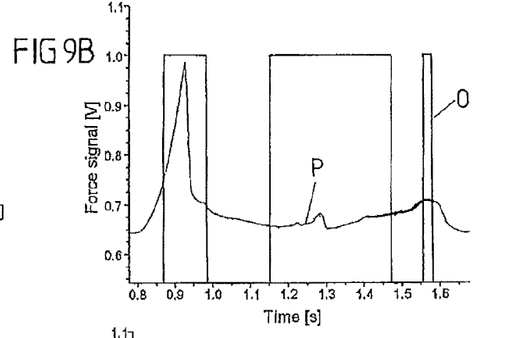
FIG. 9B shows a pressure signal associated with the seventh state.

In a seventh state, shown in FIG. 9A, the compression means 5 is moved in a direction X6 to release the flexible tube 2 such that the flexible tube 2, due to its resiliency, is decompressed and assumes its original, non-compressed shape. Due to the decompression of the flexible tube 2, a slight rise in the pressure signal P occurs, as shown in FIG. 9B.

Figure 10A:
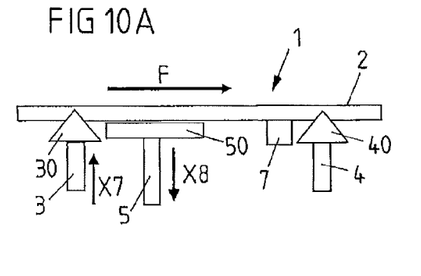
FIG. 10A shows the peristaltic pump in an eighth state.
Figure 10B:
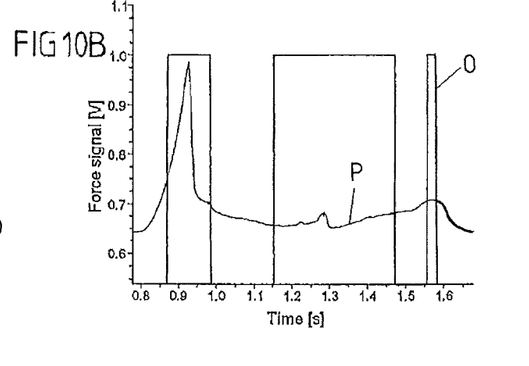
FIG. 10B shows a pressure signal associated with the eighth state.

In a tenth state, shown in FIG. 10A, finally the upstream valve means 3 is closed again by moving the upstream valve means 3 in a direction X7 to clamp off the flexible tube 2 and the compression means 5 is further moved in a direction X8 to fully release the flexible tube 2, causing a slight decrease in the pressure signal P, as indicated in FIG. 10B.

Following the eighth state according to FIG. 10A the periodic cycle starts anew, such that beginning with the first state according to FIG. 3, the compression means 5, the upstream valve means 3 and the downstream valve means 4 are actuated by the drive shaft 6 and the cams 60, 61, 62 mounted thereon in a periodical manner, hence pumping the liquid in the flow direction F through the flexible tube 2.

In FIGS. 4B-10B, both the pressure signal P and the position signal O are indicated, the position signal O representing a wave form output by the position detection means 8 due to the detection of the rotational position of the drive shaft 6 by means of the optical disc 63.

Figure 11:
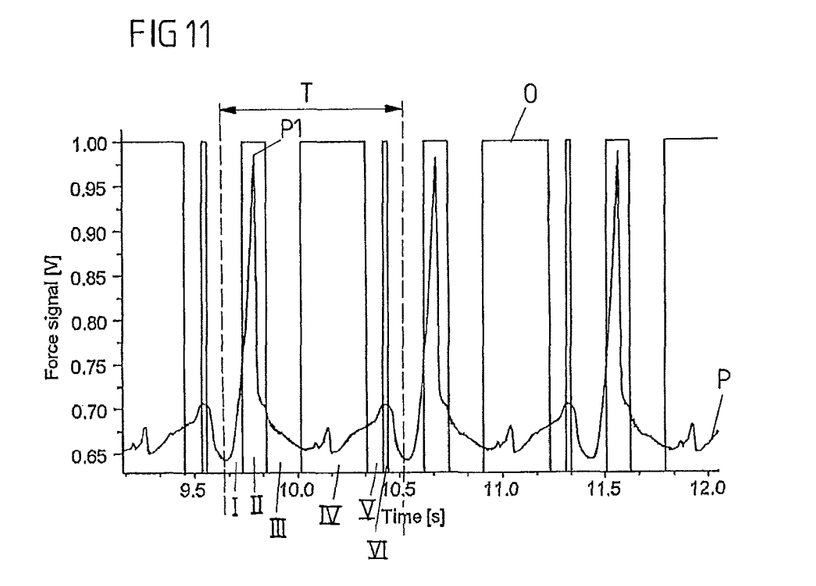
FIG. 11 shows a pressure signal measured by a pressure sensor and a position signal measured by a position detection means over multiple rotations of the drive shaft.

FIG. 11 shows in another diagrammatic view the pressure signal P and the position signal O over multiple cycles of operation of the peristaltic pump 1. Both the pressure signal P and the position signal O are periodic having a period T corresponding to one revolution of the drive shaft 6.

Figure 12:
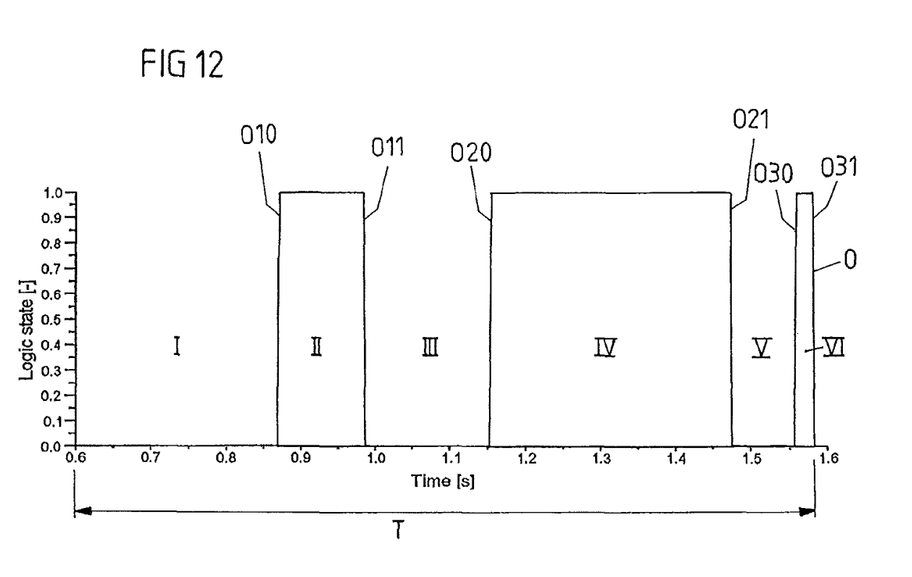
FIG. 12 shows the position signal in a separate diagrammatic view.
Figure 13A:
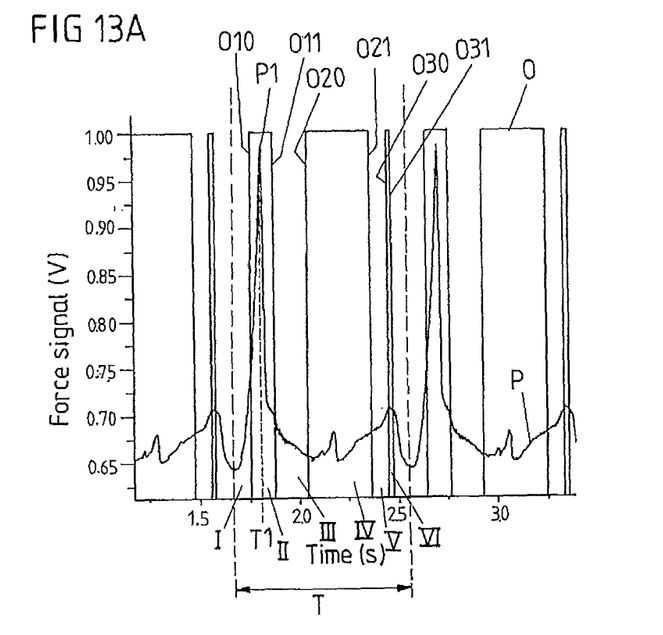
FIG. 13A shows the pressure signal and the position signal for a first set-up of the peristaltic pump.
Figure 13B:
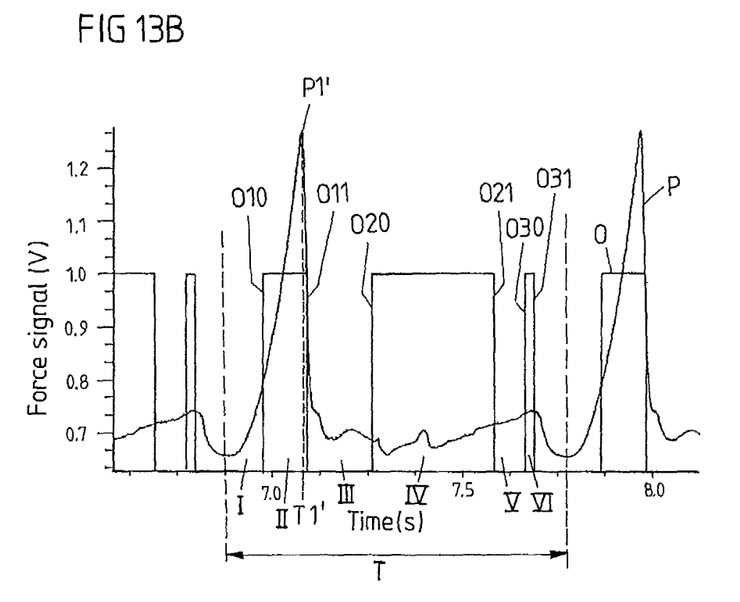
FIG. 13B shows the pressure signal and the position signal for a second set-up of the peristaltic pump.

FIG. 12 shows in a separate diagrammatic view the position signal O over one period T, and FIG. 13A, 13B show pressure signals P originating from different set-ups of the peristaltic pump 1.

As visible from FIG. 12, the position signal O is represented by a wave form which, throughout one period T corresponding to one revolution of the drive shaft 6, exhibits six intervals I, II, III, IV, V, VI defined and distinguished by rising and falling edges O10, O20, O21, O30, O31 of the position signal O. By means of the position signal O, hence, six intervals I, II, III, IV, V, VI corresponding to fractions of the period P during one revolution of the drive shaft 6 are defined, which can be used to analyse the pressure signal P for example to detect a fault condition such as an upstream occlusion or a downstream occlusion of the flexible tube 2 or an empty-bag condition occurring when a bag supplying liquid to the flexible tube 2 is empty.

The interval II, for example, corresponds to the second and third state as described above according to FIGS. 4A, 4B and 5A, 5B during which the flexible tube 2 is compressed and then opened in the downstream direction leading to the formation of a peak P1.

In the interval III, corresponding to the forth state described above according to FIGS. 6A, 6B, the downstream valve means 4 is opened such that the pressure signal P approximately indicates the pressure in the flexible tube 2 downstream of the downstream valve means 4.

And in the interval V, corresponding to the seventh state described above according to FIGS. 9A, 9B, the downstream valve means 4 is closed and the upstream valve means 3 is opened such that the pressure signal P approximately indicates an upstream pressure upstream of the upstream valve means 3.

By evaluating the pressure signal P in predefined intervals, fault conditions during operation of the peristaltic pump 1 can be determined.

In particular, an empty-bag condition can be detected by observing and detecting the peak P1 of the pressure signal P within the interval II of the position signal O. For this, the signal value of the pressure signal P at the peak P1 is recorded and is compared to the mean value of the pressure signal P during interval V, the mean value being used as a reference and corresponding to an upstream pressure value. For detecting an empty-bag condition, from the signal value at the peak P1 the mean value of the pressure signal P in the interval V is subtracted to form the difference and to obtain a measure for the peak height. This difference is then compared to a preset threshold value, and if the difference falls below the threshold value, an empty-bag alarm is raised.

FIGS. 13A and 13B show the pressure signal P for different set-ups of the peristaltic pump 1 using for example different support plates 10 (see FIG. 1) forming a rest for the flexible tube 2 and having a strong influence both on the clamping by the valve means 3, 4 and on the compression by the compression means 5. As can be seen when comparing FIGS. 13A and 13B, when changing the set-up of the peristaltic pump 1, the pressure signal P in particular in the region of the peak P1, P1' may change such that a peak P1, P1' having a different signal value and a different location T1, T1' with respect to the edges O10, O11 of the interval II arises.

Because the signal value of the peak P1, P1' and the location T1, T1' of the peak may change depending for example on the set-up of the peristaltic pump 1, it may be difficult to set a predefined fixed threshold value for determining whether an empty-bag condition is present or not, and whether an alarm should be raised or not.

To overcome this difficulty, it is made use of the finding that a change in the signal value at the peak P1, P1' is correlated to a change of the location T1, T1' of the peak P1, P1' within the interval II of the position signal O. Hence, by taking both the signal value and the location T1, T1' of the peak P1, P1' into account, one may scale the signal value to allow for a more reliable comparison to a threshold value.

For scaling the signal value at the peak P1, P1', a correction factor may be determined as a function of the location T1, T1' of the peak P1, P1' in the interval II. For determining the correction factor as a function of the location T1, T1', a linear function of the general scheme $$f(X)=AX+B$$

may be used translating the peak's location X into the correction factor f.

The coefficients A and B, herein, may for example be determined using a least squares optimisation using the scheme outlined in the following:

In a first step, for example in an initial configuration routine, the signal values and peak locations for three different set-ups (for example using different support plates 10) of the peristaltic pump 1 are recorded.

Using such parameter pairs, then, a least square optimisation may be performed which can be formulated as a minimization problem of the following equation:

$$G(A,B)=(Y_1 f(X_1)-Y_0)^2+(Y_2 f(X_2)-Y_0)^2+(Y_3 f(X_3)-Y_0)^2,$$

X1, Y1, X2, Y2 and X3, Y3 herein represent the three different parameter pairs resulting from the initial measurement (X1, X2, X3 indicating the peak's locations T1, T1' for three different set-ups and Y1, Y2, Y3 indicating the signal value of the pressure signal P at the respective peaks P1, P1'). Y0 represents a predefined value of the signal which is independent of the peak location.

By calculating the first derivatives of G, one obtains $$\frac{\partial G}{\partial A} = 2(Y_1 f(X_1)-Y_0)Y_1 X_1 + 2(Y_2 f(X_2)-Y_0)Y_2 X_2 +$$
$$2(Y_3 f(X_3)-Y_0)Y_3 X_3,$$
$$= 2((Y_1 X_1)^2+(Y_2 X_2)^2+(Y_3 X_3)^2)A +$$
$$2(Y_1^2 X_1 + Y_2^2 X_2 + Y_3^2 X_3)B -$$
$$2(Y_1 X_1 + Y_2 X_2 + Y_3 X_3)Y_0.$$

-continued $$\frac{\partial G}{\partial B} = 2(Y_1 f(X_1)-Y_0)Y_1 + 2(Y_2 f(X_2)-Y_0)Y_2 +$$
$$2(Y_3 f(X_3)-Y_0)Y_3,$$
$$= 2((Y_1^2 X_1 + Y_2^2 X_2 + Y_3^2 X_3)A + 2(Y_1^2 + Y_2^2 + Y_3^2)B -$$
$$2(Y_1 + Y_2 + Y_3)Y_0.$$

The minimum is found using $$\frac{\partial G}{\partial A} = 0$$

and $$\frac{\partial G}{\partial B} = 0.$$

Setting $$u=(Y_1 X_1)^2+(Y_2 X_2)^2+(Y_3 X_3)^2,$$

$$v=Y_1^2 X_1+Y_2^2 X_2+Y_3^2 X_3,$$

$$w=Y_1^2+Y_2^2+Y_3^2,$$

$$q=Y_1 X_1+Y_2 X_2+Y_3 X_3 \text{ and}$$

$$t=Y_1+Y_2+Y_3$$

A and B are solutions of $$\begin{cases} uA + vB = qY_0, \\ vA + wB = tY_0. \end{cases}$$

Solving this system of equations yields $$A = \frac{wq - vt}{wu - v^2} Y_0$$

and $$B = \frac{tu - vq}{wu - v^2} Y_0.$$

Thus, determining the coefficients A and B beforehand for example using three initial measurements for configuring the routine, during operation of the peristaltic pump 1, the signal value at the peak P1, P1' may be scaled using the correction factor f computed from an actual location T1, T1' of the peak P1, P1', and the scaled signal value may be compared to a preset threshold value.

In this way the detection of an empty-bag condition may be achieved in a more reliable way, because due to the scaling of the signal value at the peak P1, P1' the variation of the signal value at the peak P1, P1' for different set-ups (for example for different support plates 10) and for different mechanical conditions of the peristaltic pump 1 can be reduced.

Another fault condition that may be detected is the presence of an upstream occlusion or a downstream occlusion preventing a flow of liquid through the flexible tube 2.

In this regard, to detect for example a downstream occlusion, the downstream pressure is determined as a mean value of the pressure signal P in the interval III (defined by the edges O11, O20) and is compared to an upstream pressure determined as a mean value of the pressure signal P in the interval V (defined by the edges O21, O30), thus taking the upstream pressure as a reference.

By observing the downstream pressure for continuous cycles during operation of the peristaltic pump 1 and comparing it to the upstream pressure as a reference, a downstream occlusion may be detected in a reliable manner, because the effects of altering mechanical conditions or temperature changes are present both in the upstream pressure and the downstream pressure, and, thus, can be eliminated by using the upstream pressure as a reference.

If the relation between the downstream pressure and the upstream pressure falls below a predetermined level, it is concluded that an occlusion situation is present. Then, before triggering an alarm, further revolutions of the drive shaft 6 are performed to determine whether a downstream occlusion (recognized from a rise in the downstream pressure from revolution to revolution, or from observing the difference between the downstream pressure and the upstream pressure and triggering an alarm if the difference is higher than for example 1 bar) or an upstream occlusion (if the occlusion is not downstream then it is necessarily upstream) is present.

The idea underlying the invention is not limited to the embodiments described above. In particular, the pressure signal and the position signal determined by appropriate sensors and detection means within a peristaltic pump may have an entirely different shape such that algorithms applied for detecting a fault condition may be adopted accordingly using the principles outlined herein.

A peristaltic pump of the kind described herein may in particular be used for the delivery of liquid nutriments for the enteral feeding of patients in a hospital environment. However, the application of a peristaltic pump of the noted kind is not limited to this specific purpose, but the peristaltic pump may be used also for a delivery of any other liquid such as blood or other medical solutions.

LIST OF REFERENCE NUMERALS

1 Peristaltic pump
10 Support plate (door)
2 Tube
3, 4 Valve means (clamp finger)
30, 40 Finger head
5 Compression means (pump finger)
50 Finger head
6 Drive shaft
60-62 Cam
63 Optical disc
7 Pressure sensor
8 Position detection means
9 Control means
F Flow direction
O Position signal
O10, O11, O20, O21, O30, O31 Edge
P Pressure signal
P1, P1' Peak
R Direction of rotation
T Period
T1, T1' Peak location
X1-X8 Direction of motion
I-VI Interval

The invention claimed is:

1. A peristaltic pump for pumping a liquid, comprising:
    a flexible tube for guiding the liquid to be pumped,
    a finger head being actuatable for compressing the flexible tube,
    an upstream valve arranged in an upstream direction with respect to the finger head and being actuatable to selectively open or close the flexible tube upstream of the finger head,
    a downstream valve arranged in a downstream direction with respect to the finger head and being actuatable to selectively open or close the flexible tube downstream of the finger head,
    a drive shaft being rotatable for periodically actuating the finger head, the upstream valve and the downstream valve,
    a position detector for detecting the rotational position of the drive shaft during actuation of the finger head, the upstream valve and the downstream valve,
    a pressure sensor being arranged between the upstream valve and the downstream valve for measuring a pressure signal (P) in the flexible tube at a location between the upstream valve and the downstream valve, and
    a controller to control the operation of the peristaltic pump, the controller being operative to detect a fault condition during the operation of the peristaltic pump from a measured pressure signal (P),
    wherein the controller for detecting the fault condition is operative to detect a peak (P1, P1') of the pressure signal (P) in a predefined interval (II) during rotation of the drive shaft and to determine whether the fault condition is present or not by taking a value of the signal at a peak (P1, P1') and a location (T1, T1') of the peak (P1, P1') in the predefined interval (II) into account, the signal value at the peak (P1, P1') is multiplied by a factor and related to a reference value, wherein the factor is computed using the location (T1, T1') of the peak (P1, P1') in the predefined interval (II).

2. The peristaltic pump according to claim 1, wherein the controller is operative to detect, as fault condition, whether liquid is supplied to the tube upstream of the upstream valve.

3. The peristaltic pump according to claim 1, wherein during a first portion of the predefined interval (II), both the upstream valve and the downstream valve are closed and the finger head is actuated to compress the flexible tube.

4. The peristaltic pump according to claim 3, wherein during a second portion of the predefined interval (II) the downstream valve is opened to open the flexible tube.

5. The peristaltic pump according to claim 1 wherein the drive shaft carries a disc acting together with the position detection means and indicating intervals (I-VI) during rotation of the drive shaft for periodically actuating the finger head, the upstream valve and the downstream valve.

6. The peristaltic pump according to claim 1, wherein the reference value is determined from a mean value of the pressure signal (P) during an interval (V) of the rotation of the drive shaft during which the upstream valve is opened and the downstream valve is closed.

7. The peristaltic pump according to claim 1 wherein to determine whether the fault condition is present or not, the difference between the signal value at the peak (P1, P1') and the reference value is formed to determine a peak height, wherein the peak height is compared to a threshold value to determine whether the fault condition is present or not.

8. The peristaltic pump according to claim 1, wherein
    an upstream pressure value is determined from a mean value of the pressure signal (P) during an interval (V) of the rotation of the drive shaft during which the upstream valve is opened and the downstream valve is closed and
    a downstream pressure value is determined from a mean value of the pressure signal (P) during an interval (III)

of the rotation of the drive shaft during which the upstream valve is closed and the downstream valve is opened, wherein for detecting an occlusion of the flexible tube upstream of the upstream valve and/or downstream of the downstream valve the upstream pressure value and the downstream pressure value are compared to each other.

9. A method for operating the peristaltic pump of claim 1 for pumping a liquid comprising:

detecting the fault condition by detecting with the controller a peak (P1, P1') of the pressure signal (P) in a predefined interval (II) during rotation of the drive shaft and determines whether the fault condition is present or not by taking the signal value at the peak (P1, P1') and the location (T1, T1') of the peak (P1, P1') in the predefined interval (II) into account.

* * * * *